United States Patent [19]

Saeki et al.

[11] Patent Number: 4,965,395
[45] Date of Patent: Oct. 23, 1990

[54] P-OXYBENZOIC ACID COMPOUNDS

[75] Inventors: Kazumi Saeki; Takeshi Inoue; Shoichi Horie, all of Nakatsu, Japan

[73] Assignee: Yoshitomi Pharmaceutical Industries, Ltd., Osaka, Japan

[21] Appl. No.: 324,569

[22] Filed: Mar. 16, 1989

Related U.S. Application Data

[63] Continuation of Ser. No. 125,351, Nov. 25, 1987, abandoned, which is a continuation of Ser. No. 10,090, filed as PCT JP86/00265 on May 23, 1986, published as WO86/07052 on Dec. 4, 1986, abandoned.

[30] Foreign Application Priority Data

May 27, 1985 [JP]  Japan ............................... 60-113867

[51] Int. Cl.$^5$ ............................................. C07C 149/40
[52] U.S. Cl. ......................................... 560/11; 560/18; 514/533
[58] Field of Search ....................................... 560/11, 18

[56] References Cited

FOREIGN PATENT DOCUMENTS 532353  9/1981  Australia .
1768146  7/1972  Fed. Rep. of Germany .

OTHER PUBLICATIONS

Denisova, Khim–Farm. Zh., 15, pp. 33–36 (1981).

Primary Examiner—Michael L. Shippen
Attorney, Agent, or Firm—Wenderoth, Lind and Ponack

[57] ABSTRACT p-Oxybenzoic acid compounds of the general formula:

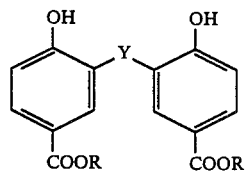

wherein R is alkyl having not less than two carbon atoms or aralkyl and Y is sulfur atom or sulfonyl.

The compounds exhibit bactericidal activity and are useful as bactericides.

3 Claims, No Drawings

P-OXYBENZOIC ACID COMPOUNDS

This application is a continuation of now abandoned application Ser. No. 125,351, filed Nov. 25, 1987, which is a continuation of now abandoned application Ser. No. 010,090, filed as PCT JP86/00265 on May 23, 1986, published as WO86/07052 on Dec. 4, 1986.

TECHNICAL FIELD

The present invention relates to novel and industrially useful p-oxybenzoic acid compounds.

BACKGROUND OF THE INVENTION

It is well known that p-oxybenzoic acid ester compounds are used as industrial chemicals. Particularly, the lower alkyl ester compounds exhibit antibacterial and antiseptic effects, and are widely used as industrial antibacterials. Further, it is known that 3,3'-thiobis(methyl 4-hydroxybenzoate) can be obtained by reacting methyl p-hydroxybenzoate with sulfur monochloride and can be converted into the corresponding sulfoxide and sulphone compounds by the oxidation according to Khim-Farm. Zh., Vol. 15(1) pages 33-36 (1981) (c.f. Chemical Abstracts, Vol. 95(1) 6734a, 1981). However, this reference describes 3,3'-thiobis(methyl 4-hydroxybenzoate) and sulfoxide of said compound are inactive against Fasciola in rats and rabbits.

DISCLOSURE OF THE INVENTION

The present inventors have intensively investigated in order to develop industrially useful and novel compounds. As a result of such investigations, the present inventors have completed the present invention. Namely, the present invention relates to p-oxybenzoic acid compounds represented by the general formula:

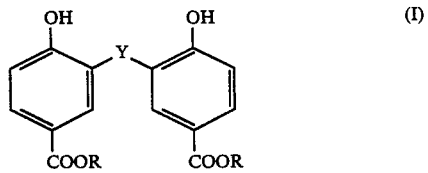

wherein R is alkyl having not less than two carbon atoms (e.g. ethyl, propyl, isopropyl, butyl, isobutyl, sec-butyl, tert-butyl, pentyl, isopentyl, neopentyl, hexyl, heptyl, octyl, 2-ethylhexyl, sec-octyl, tert-octyl, nonyl, decyl, undecyl, dodecyl, tridecyl, tetradecyl, sec-tetradecyl, pentadecyl, hexadecyl, sec-hexadecyl, heptadecyl, octadecyl, nonadecyl, eicosyl, docosyl, tetracosyl, hexacosyl or octacosyl) or aralkyl (especially, phenylalkyl which has generally 1-6 carbon atoms in the alkyl moiety such as benzyl, 2-phenylethyl, 3-phenylpropyl, 4-phenylbutyl, 5-phenylpentyl or 6-phenylhexyl) and Y is sulfur atom and sulfonyl.

The preferable compounds of the present invention are the compounds wherein R is alkyl having 2-22 carbon atoms or benzyl, and are exemplified in detail as follows:
3,3'-thiobis(ethyl p-hydroxybenzoate)
3,3'-sulfonylbis(ethyl p-hydroxybenzoate)
3,3'-thiobis(propyl p-hydroxybenzoate)
3,3'-sulfonylbis(propyl p-hydroxybenzoate)
3,3'-thiobis(butyl p-hydroxybenzoate)
3,3'-sulfonylbis(butyl p-hydroxybenzoate)
3,3'-thiobis(hexyl p-hydroxybenzoate)
3,3'-thiobis(2-ethylhexyl p-hydroxybenzoate)
3,3'-sulfonylbis(2-ethylhexyl p-hydroxybenzoate)
3,3'-thiobis(dodecyl p-hydroxybenzate)
3,3'-thiobis(tetradodecyl p-hydroxybenzoate)
3,3'-thiobis(hexadecyl p-hydroxybenzoate)
3,3'-sulfonylbis(hexadecyl p-hydroxybenzoate)
3,3'-thiobis(octadecyl p-hydroxybenzoate)
3,3'-sulfonylbis(octadecyl p-hydroxybenzoate)
3,3'-thiobis(docosyl p-hydroxybenzoate)
3,3'-sulfonylbis(docosyl p-hydroxybenzoate)
3,3'-thiobis(benzyl p-hydroxybenzoate)

The p-oxybenzoic acid compounds of formula (I), for example, can be produced according to the following methods:

(1) The compounds wherein Y is sulfur atom, can be produced by reacting the compound of the general formula:

wherein R is as defined above, with a sulfur compound.

The sulfur compound includes, for example, sulfur as a simple substance, sulfur monochloride or sulfur dichloride.

The reaction is usually carried out in a suitable solvent (e.g. methylene chloride, dichloroethane, chloroform, tetrachloromethane, tetrachloroethane, acetic acid or carbon disulfide) in the presence of an acidic catalyst (e.g. sulfuric acid, boron trifluoride, tin tetrachloride, alminium chloride, zinc chloride, trifluoroacetic acid, pyridine hydrochloride, a complex of pyridine with sulfuric acid anhydrate) at about −20° C. to about 150° C., preferably at about 0° C. to about 40° C. The acidic catalyst is usually used in the range of about 0.01-10 mole to one mole of the compound of formula (II).

(2) The compounds wherein Y is sulfonyl, can be produced by subjecting the compound wherein Y is sulfur produced according to method (1) to oxidative reaction. The oxidant usable in the oxidative reaction includes per acids such as hydrogen peroxide, peracetic acid or perbenzoic acid, or inorganic oxidant such as potassium permanganate or potassium periodate, but they are not to be construed as limiting the oxidant to be used in the present invention.

The reaction is usually carried out in an inert solvent (preferably, a polar solvent such as acetone, methanol or acetic acid) at about −20° C. to about 120° C., preferably at about 0° C. to about 100° C.

The compounds thus obtained can be purified by a conventional manner such as column chromatography or recrystallization.

The compounds of the present invention exhibit bactericidal activity, and are useful, especially, as industrial bactericides.

As a result of the test of bactericidal activity of the compounds of the present invention, the present inventors have found that the solubility and surface tension of the compounds of the present invention against water are lowered with the increase of the number of carbon atoms of the ester moiety, and the compounds of the present invention exhibit much more excellent bactericidal action, compared with conventional methyl ester compounds.

The compounds of the present invention exert a noticeable bactericidal effect on industrially harmful microbes, specifically bacteria such as those of the genus Bacillus and those of the genus Staphylococcus.

The compounds of the present invention are very useful for the purpose of protecting, for example, various materials for industrial use and industrial products from microbial damages.

The compounds of the present invention are useful in preventing:

(1) harms on products of wood, plywood, etc. and on themselves, such as staining due to bacterial growth, and (2) decomposition and deterioration of aqueous emulsion paints during storage or transportation due to bacterial growth, and contaminative harms on paint film surfaces after application of aqueous emulsion paints due to bacterial growth.

The compounds of the present invention may be used alone, and may also be used as oil solutions, wettable powders, dusts, emulsions, etc., in combination with an appropriate carrier, diluent and dust diluent, or in the presence of additives such as dispersing agent, penetrating agent and wetting agent. The amounts of the compounds of the present invention to be incorporated in said preparations preferably range from 0.1 to 50% by weight.

As examples of such carriers, mention may be made of clay, kaolin, bentonite, acid clay, diatomaceous earth, calcium carbonate, starch, gum arabic, benzene, xylene, alcohol, acetone, kerosene, dimethylformamide, etc. In addition, as surface active agents for generally used adjuvants in preparation process, such as spreaders, emulsifiers, dispersing agents, etc., soap, sulfuric acid esters of higher alcohols, alkyl sulfonates, alkylarylsulfonates, quaternary ammonium salts, polyalkylene oxides, etc. may also be added as appropriate.

The compounds of the present invention, when used as bactericides, can be used alone or combined with not less than two compounds of the present invention. Moreover, the compounds of the present invention can be combined with conventional bactericidal compounds.

In using the compounds of the present invention as bactericides for wood, plywood, aqueous emulsion paints or other articles to be treated, conventional means such as painting, spraying, dipping, mixing, etc., selected according to types of articles to be treated, purposes of application, etc., can be employed as appropriate. It is normally preferable that the compounds of the present invention are applied in the manner that their final concentrations will be between about 0.5 ppm and about 500 ppm, though the application rates of the compounds of the present invention depend upon types of bacteria, types of articles to be applied, application environments, etc.

EXPERIMENTAL EXAMPLE 1

Minimum inhibitory concentration test

One part of the subject compound was dissolved in 9 parts of dimethylformamide. Using this solution, determinations were made of the minimum inhibitory concentrations for various microbes by the agar dilution method. The results are shown in the following table.

| Subject compound | Subject microbes and minimum inhibitory concentrations ($\mu$g/ml) | |
|---|---|---|
| | Staphylococcus aureus | Bacillus subtilis |
| Compounds of the present invention | | |
| 3,3'-thiobis (propyl p-hydroxybenzoate) | 7.8 | 4.0 |
| 3,3'-thiobis (benzyl p-hydroxybenzoate) | 7.8 | 2.0 |
| 3,3'sulfonylbis (butyl p-hydroxybenzoate) | 7.8 | 2.0 |
| 3,3'-thiobis (docosyl p-hyroxybenzoate) | 7.8 | 4.0 |
| 3,3'-sulfonylbis (docosyl p-hydroxybenzoate) | 7.8 | 4.0 |
| Conventional compounds | | |
| 3,3'-sulfinylbis (methyl p-hydroxybenzoate | 500 | 250 |
| 3,3'-thiobis (methyl p-hydroxybenzoate) | 31.3 | 31.3 |

The following examples will explain the present invention in more detail, but they are not to be construed as limiting the present invention. The compounds obtained were identified to be the objective compounds by means of infrared absorption spectrophotometry, nuclear magnetic resonance spectrometry, mass spectrometry or elementary analysis.

EXAMPLE 1

To a suspension of 33.2 g of ethyl p-hydroxybenzoate, 100 ml of dichloroethane and 0.5 g of zinc chloride anhydrate is added a solution of 13.5 g of sulfur monochloride in 50 ml of dichloroethane at 20° C. and stirred at 40° C. for 4 hours. After standing at room temperature, the precipitated crystals are collected by filtration and washed with dichloroethane, water and then chloroform in turn to give 3,3'-thiobis(ethyl p-hydroxybenzoate) as white crystals, melting at 156°–159° C. The product is recrystallized from acetic acid to give white crystals, melting at 177°–178.5° C.

EXAMPLE 2

To a solution of 5 g of 3,3'-thiobis(ethyl p-hydroxybenzoate) in 50 ml of acetic acid is gradually added 18 g of 30% hydrogen peroxide at 70°–80° C. and further stirred at the same temperature for 2 hours. A small amount of the product is filtered off and, after addition of water, the filtrate is repeatedly concentrated. The precipitated crystals are collected by filtration to give 4.3 g of 3,3'-sulfonylbis(ethyl p-hydroxybenzoate) monohydrate, melting at 155°–156° C. The product is recrystallized from ethyl acetate to give the corresponding anhydrate, melting at 166°–168° C.

EXAMPLE 3

To a suspension of 36 g of propyl p-hydroxybenzoate, 100 ml of chloroform and 0.5 g of zinc chloride anhydrate is added a solution of 13.5 g of sulfur monochloride in 50 ml of chloroform and the reaction is conducted according to the same manner as described in Example 1. The obtained crude crystals are recrystallized from acetic acid to give 3,3'-thiobis(propyl p-hydroxybenzoate) as a white powder, melting at 145°–148° C.

EXAMPLE 4

A solution of 15 g of 3,3'-thiobis(propyl p-hydroxybenzoate) in 40 ml of acetic acid is reacted with 45 g of 30% hydrogen peroxide in the same manner as described in Example 2 to give 3,3'-sulfonylbis(propyl p-hydroxybenzoate) dihydrate, melting at 109° C. The product is recrystallized from acetic acid to give the corresponding anhydrate, melting at 185° C.

EXAMPLE 5

To a mixture of isopropyl p-hydroxybenzoate, dichloroethane and zinc chloride anhydrate is added a solution of sulfur monochloride in dichloroethane and stirred under heating. The reaction mixture is treated in the same manner as described in the above Examples to give 3,3'-thiobis(isopropyl p-hydroxybenzoate). Further, to a solution of the product thus obtained in acetic acid is gradually added 30% hydrogen peroxide at 70°–80° C. and stirred at the same temperature for 1–2 hours. After completion of the reaction, the product is separated and, if necessary, purified to give 3,3'-sulfonylbis(isopropyl p-hydroxybenzoate).

EXAMPLE 6

To a suspension of 38.8 g of butyl p-hydroxybenzoate, 70 ml of dichloroethane and 1.3 g of zinc chloride anhydrate is added a solution of 15 g of sulfur monochloride in 30 ml of dichloroethane and stirred in the same manner as described in Example 1. The obtained reaction solution is washed with an aqueous sodium bicarbonate solution and then water, and further the dichloroethane is distilled off to give pale yellow oil. The oil thus obtained is purified by a silica gel column chromatography with chloroform to give 3,3'thiobis(-butyl p-hydroxybenzoate), melting at 108°–109° C.

EXAMPLE 7

A solution of 34 g of 3,3'-thiobis(butyl p-hydroxybenzoate) in 150 ml of acetic acid is reacted with 41 ml of 30% hydrogen peroxide in the same manner as described in Example 2. The obtained crude crystals are purified by a silica gel column chromatography with chloroform to give 3,3'-sulfonylbis(butyl p-hydroxybenzoate), melting at 109°–112° C.

EXAMPLE 8

To a mixture of isobutyl p-hydroxybenzoate, dichloroethane and zinc chloride anhydrate is added a solution of sulfur monochloride in dichloroethane and stirred under heating. The reaction mixture is treated in the same manner as described in the above Examples to give 3,3'-thiobis(isobutyl p-hydroxybenzoate). Further, to a solution of the product thus obtained in acetic acid is gradually added 30% hydrogen peroxide at 70°–80° C. and stirred at the same temperature for 1–2 hours. After completion of the reaction, the product is separated and, if necessary, purified to give 3,3'-sulfonylbis(isobutyl p-hydroxybenzoate).

EXAMPLE 9

To a mixture of sec-butyl p-hydroxybenzoate, dichloroethane and zinc chloride anhydrate is added a solution of sulfur monochloride in dichloroethane and stirred under heating. The reaction mixture is treated in the same manner as described in the above Examples to give 3,3'-thiobis(sec-butyl p-hydroxybenzoate). Further, to a solution of the product thus obtained in acetic acid is gradually added 30% hydrogen peroxide at 70°–80° C. and stirred at the same temperature for 1–2 hours. After completion of the reaction, the product is separated and, if necessary, purified to give 3,3'-sulfonylbis(secbutyl p-hydroxybenzoate).

EXAMPLE 10

To a mixture of pentyl p-hydroxybenzoate, dichloroethane and zinc chloride anhydrate is added a solution of sulfur monochloride in dichloroethane and stirred under heating. The reaction mixture is treated in the same manner as described in the above Examples to give 3,3'-thiobis(pentyl p-hydroxybenzoate). Further, to a solution of the product thus obtained in acetic acid is gradually added 30% hydrogen peroxide at 70°–80° C. and stirred at the same temperature for 1–2 hours. After completion of the reaction, the product is separated and, if necessary, purified to give 3,3'-sulfonylbis(-pentyl p-hydroxybenzoate).

EXAMPLE 11

To a mixture of isopentyl p-hydroxybenzoate, dichloroethane and zinc chloride anhydrate is added a solution of sulfur monochloride in dichloroethane and stirred under heating. The reaction mixture is treated in the same manner as described in the above Examples to give 3,3'-thiobis(isopentyl p-hydroxybenzoate). Further, to a solution of the product thus obtained in acetic acid is gradually added 30% hydrogen peroxide at 70°–80° C. and stirred at the same temperature for 1–2 hours. After completion of the reaction, the product is separated and, if necessary, purified to give 3,3'-sulfonylbis(isopentyl p-hydroxybenzoate).

EXAMPLE 12

To a solution of 98 g of hexyl p-hydroxybenzoate, 150 ml of chloroform and 0.5 g of zinc chloride anhydrate is added a solution of 32.7 g of sulfur monochloride in 100 ml of chloroform at 18°–20° C. and stirred at 40° C. for 5 hours. After distilling off the chloroform, a solution of the residue thus obtained in toluene is washed with water, 3N hydrochloric acid, an aqueous sodium bicarbonate solution and an aqueous sodium chloride solution. Subsequently, the toluene is distilled off and the oil thus obtained is purified by a silica gel column chromatography with chloroform to give 3,3'-thiobis(hexyl p-hydroxybenzoate) as a viscous oil. Then, to a solution of the viscous oil obtained in acetic acid is added 30% hydrogen peroxide and stirred at the same temperature for several hours. After the concentration of the reaction mixture, the obtained oil is purified by a silica gel column chromatography to give 3,3'-sulfonylbis(hexyl p-hydroxybenzoate).

EXAMPLE 13

To a mixture of heptyl p-hydroxybenzoate, dichloroethane and zinc chloride anhydrate is added a solution of sulfur monochloride in dichloroethane and stirred under heating. The reaction mixture is treated in the same manner as described in the above Examples to give 3,3'-thiobis(heptyl p-hydroxybenzoate). Further, to a solution of the product thus obtained in acetic acid is gradually added 30% hydrogen peroxide at 70°–80° C. and stirred at the same temperature for 1–2 hours. After completion of the reaction, the product is separated and, if necessary, purified to give 3,3'-sulfonylbis(-heptyl p-hydroxybenzoate).

EXAMPLE 14

To a mixture of octyl p-hydroxybenzoate, dichloroethane and zinc chloride anhydrate is added a solution of sulfur monochloride in dichloroethane and stirred under heating. The reaction mixture is treated in the same manner as described in the above Examples to give 3,3'-thiobis (octyl p-hydroxybenzoate). Further, to a solution of the product thus obtained in acetic acid is gradually added 30% hydrogen peroxide at 70°-80° C. and stirred at the same temperature for 1-2 hours. After completion of the reaction, the product is separated and, if necessary, purified to give 3,3'-sulfonylbis(octyl p-hydroxybenzoate).

EXAMPLE 15

To a solution of 50 g of 2-ethylhexyl p-hydroxybenzoate, 100 ml of chloroform and 0.5 g of zinc chloride anhydrate is added a solution of 15 g of sulfur monochloride in 50 ml of chloroform at 15°-20° C. and stirred at 40° C. for 5 hours. The reaction mixture is treated in the same manner in Example 12 to give 3,3'-thiobis(2-ethylhexyl p-hydroxybenzoate) as an oil. Then, to a solution of 20 g of the oil thus obtained in 50 ml of acetic acid is added 60 ml of 30% hydrogen peroxide at 70°-80° C. over 4 hours, and further stirred at the same temperature for 4 hours. After the addition of water, the mixture is repeatedly concentrated. A solution of the residue thus obtained in ethyl acetate is washed with an aqueous sodium bicarbonate solution and an aqueous sodium chloride solution, and then the ethyl acetate is distilled off to give oil. The oil thus obtained is purified by a silica gel column chromatography with chloroform to give 3,3'-sulfonylbis(2-ethylhexyl p-hydroxybenzoate) as a viscous oil.

EXAMPLE 16

To a mixture of sec-octyl p-hydroxybenzoate, dichloroethane and zinc chloride anhydrate is added a solution of sulfur monochloride and stirred under heating. The reaction mixture is treated in the same manner as described in the above Examples to give 3,3'-thiobis(-sec-octyl p-hydroxybenzoate). Further, to a solution of the product thus obtained in acetic acid is gradually added 30% hydrogen peroxide at 70°-80° C. and stirred at the same temperature for 1-2 hours. After completion of the reaction, the product is separated and, if necessary, purified to give 3,3'-sulfonylbis(sec-octyl p-hydroxybenzoate).

EXAMPLE 17

To a mixture of decyl p-hydroxybenzoate, dichloroethane and zinc chloride anhydrate is added a solution of sulfur monochloride in dichloroethane and stirred under heating. The reaction mixture is treated in the same manner as described in the above Examples to give 3,3'-thiobis(decyl p-hydroxybenzoate). Further, to a solution of the product thus obtained in acetic acid is gradually added 30% hydrogen peroxide at 70°-80° C. and stirred at the same temperature for 1-2 hours. After completion of the reaction, the product is separated and, if necessary, purified to give 3,3'-sulfonylbis(decyl p-hydroxybenzoate).

EXAMPLE 18

To a solution of 15.3 g of dodecyl p-hydroxybenzoate, 100 ml of dichloroethane and 0.3 g of zinc chloride anhydrate is added a solution of 3.7 g of sulfur monochloride in 30 ml of dichloroethane at 20° C. and stirred at 40° C. for 8 hours. After washing with water, the dichloroethane is distilled off and the obtained residue is dissolved in methanol under heating. After cooling, the precipitated sulfur is filtered off and then the methanol is distilled off. The residue is crystallized from ethanol, and then the obtained crystals are collected by filtration and recrystallized from hexane to give 3,3'-thiobis(-dodecyl p-hydroxybenzoate) as a white powder, melting at 72°-74° C. Further, to a solution of the product thus obtained in acetic acid is added 30% hydrogen peroxide at 70°-80° C. and stirred at the same temperature for several hours. After completion of the reaction, the product is separated and, if necessary, purified to give 3,3'-sulfonylbis(dodecyl p-hydroxybenzoate).

EXAMPLE 19

To a mixture of tridecyl p-hydroxybenzoate, dichloroethane and zinc chloride anhydrate is added a solution of sulfur monochloride in dichloroethane and stirred under heating. The reaction mixture is reacted in the same manner as described in the above Examples to give 3,3'-thiobis(tridecyl p-hydroxybenzoate). Further, to a solution of the product thus obtained in acetic acid is gradually added 30% hydrogen peroxide at 70°-80° C. and stirred at the same temperature for 1-2 hours. After completion of the reaction, the product is separated and, if necessary, purified to give 3,3'-sulfonylbis(-tridecyl p-hydroxybenzoate).

EXAMPLE 20

To a solution of 16.7 g of tetradecyl p-hydroxybenzoate, 100 ml of dichloroethane and 0.3 g of zinc chloride anhydrate is added a solution of 3.7 g of sulfur monochloride in 30 ml of dichloroethane at 20° C. and stirred at 40° C. for 8 hours. After standing at room temperature, the precipitated crystals are collected by filtration and washed with dichloroethane and then methanol. The obtained crystals are recrystallized from dichloroethane to give 3,3'-thiobis(tetradecyl p-hydroxybenzoate) as a white powder, melting at 80°-81° C. Further, to a solution of the product thus obtained in acetic acid is added 30% hydrogen peroxide at 70°-80° C. and stirred at the same temperature for several hours. After completion of the reaction, the product is separated and, if necessary, purified to give 3,3'-sulfonylbis(tetradecyl p-hydroxybenzoate).

EXAMPLE 21

To a mixture of sec-tetradecyl p-hydroxybenzoate, dichloroethane and zinc chloride anhydrate is added a solution of sulfur monochloride in dichloroethane and stirred under heating. The reaction mixture is treated in the same manner as described in the above Examples to give 3,3'-thiobis(sec-tetradecyl p-hydroxybenzoate). Further, to a solution of the product thus obtained in acetic acid is gradually added 30% hydrogen peroxide at 70°-80° C. and stirred at the same temperature for 1-2 hours. After completion of the reaction, the product is separated and, if necessary, purified to give 3,3'-sulfonylbis(sec-tetradecyl p-hydroxybenzoate).

EXAMPLE 22

To a mixture of pentadecyl p-hydroxybenzoate, dichloroethane and zinc chloride anhydrate is added a solution of sulfur monochloride and stirred under heating. The reaction mixture is treated in the same manner as described in the above Examples to give 3,3'-thiobis(- pentadecyl p-hydroxybenzoate). Further, to a solution of the product thus obtained in acetic acid is gradually added 30% hydrogen peroxide at 70°–80° C. and stirred at the same temperature for 1–2 hours. After completion of the reaction, the product is separated and, if necessary, purified to give 3,3'-sulfonylbis(pentadecyl p-hydroxybenzoate).

EXAMPLE 23

To a solution of 18 g of hexadecyl p-hydroxybenzoate, 100 ml of dichloroethane and 0.3 g of zinc chloride anhydrate is added a solution of 3.7 g of sulfur monochloride in 30 ml of dichloroethane at 20° C. and stirred at 40° C. for 7 hours. After ice-cooling, the precipitated crystals are collected by filtration and washed with dichloroethane and then methanol to give 3,3'-thiobis(hexadecyl p-hydroxybenzoate) as a white powder, melting at 88°–89° C.

EXAMPLE 24

To a solution of 14 g of 3,3'-thiobis(hexadecyl p-hydroxybenzoate) in 50 ml of acetic acid is gradually added 9.1 g of 30% hydrogen peroxide at 70°–80° C. Further, the reaction mixture is stirred at the same temperature for 2 hours and then the crystals precipitated after addition of water are collected by filtration. The obtained crude crystals are purified by a silica gel column chromatography with chloroform to give 3,3'-sulfonylbis(hexadecyl p-hydroxybenzoate), melting at 34°–35° C.

EXAMPLE 25

To a mixture of sec-hexadecyl p-hydroxybenzoate, dichloroethane and zinc chloride anhydrate is added a solution of sulfur monochloride in dichloroethane and stirred under heating. The reaction mixture is treated in the same manner as described in the above Examples to give 3,3'-thiobis(sec-hexadecyl p-hydroxybenzoate). Further, to a solution of the product thus obtained in acetic acid is gradually added 30% hydrogen peroxide at 70°–80° C. and stirred at the same temperature for 1–2 hours. After completion of the reaction, the product is separated and, if necessary, purified to give 3,3'-sulfonylbis(sec-hexadecyl p-hydroxybenzoate).

EXAMPLE 26

To a mixture of heptadecyl p-hydroxybenzoate, dichloroethane and zinc chloride anhydrate is added a solution of sulfur monochloride in dichloroethane and stirred under heating. The reaction mixture is treated in the same manner as described in the above Examples to give 3,3'-thiobis(heptadecyl p-hydroxybenzoate). Further, to a solution of the product thus obtained in acetic acid is gradually added 30% hydrogen peroxide at 70°–80° C. and stirred at the same temperature for 1–2 hours. After completion of the reaction, the product is separated and, if necessary, purified to give 3,3'-sulfonylbis(heptadecyl p-hydroxybenzoate).

EXAMPLE 27

To a solution of 11.7 g of octadecyl p-hydroxybenzoate, 100 ml of dichloroethane and 0.2 g of zinc chloride anhydrate is added a solution of 2.2 g of sulfur monochloride in 20 ml of dichloroethane at 20° C. and the mixture is stirred at 40° C. for 7 hours. After standing at room temperature, the precipitated crystals are collected by filtration and washed with dichloroethane, methanol and then aqueous methanol in turn to give 3,3'-thiobis(octadecyl p-hydroxybenzoate) as a white powder, melting at 90.5°–91.5° C.

EXAMPLE 28

To a solution of 7 g of 3,3'-thiobis(octadecyl p-hydroxybenzoate) in 40 ml of acetic acid is gradually added 3.9 g of 30% hydrogen peroxide at 70°–80° C. and stirred at the same temperature for an hour. After standing at room temperature, the precipitated crystals are collected by filtration and purified by a silica gel column chromatography with chloroform to give 3,3'-sulfonylbis(octadecyl p-hydroxybenzoate), melting at 55°–57° C.

EXAMPLE 29

To a mixture of nonadecyl p-hydroxybenzoate, dichloroethane and zinc chloride anhydrate is added a solution of sulfur monochloride in dichloroethane and stirred under heating. The reaction mixture is treated in the same manner as described in the above Examples to give 3,3'-thiobis(nonadecyl p-hydroxybenzoate). Further, to a solution of the product thus obtained in acetic acid is gradually added 30% hydrogen peroxide at 70°–80° C. and stirred at the same temperature for 1–2 hours. After completion of the reaction, the product is separated and, if necessary, purified to give 3,3'-sulfonylbis(nonadecyl p-hydroxybenzoate).

EXAMPLE 30

To a mixture of eicosyl p-hydroxybenzoate, dichloroethane and zinc chloride anhydrate is added a solution of sulfur monochloride in dichloroethane and stirred under heating. The reaction mixture is treated in the same manner as described in the above Examples to give 3,3'-thiobis(eicosyl p-hydroxybenzoate). Further, to a solution of the product thus obtained in acetic acid is gradually added 30% hydrogen peroxide at 70°–80° C. and stirred at the same temperature for 1–2 hours. After completion of the reaction, the product is separated and, if necessary, purified to give 3,3'-sulfonylbis(eicosyl p-hydroxybenzoate).

EXAMPLE 31

To a suspension of 94 g of docosyl p-hydroxybenzoate, 700 ml of dichloroethane and 1 g of zinc chloride anhydrate is added a solution of 15.6 g of sulfur monochloride in 100 ml of dichloroethane at 16° C. and stirred at 40° C. for 12 hours. After cooling, the precipitated crystals are collected by filtration and washed with methanol, aqueous methanol and then methanol in turn to give 3,3'-thiobis(docosyl p-hydroxybenzoate), melting at 86°–90° C.

EXAMPLE 32

To a solution of 22.2 g of 3,3'-thiobis(docosyl p-hydroxybenzoate) in 250 ml of acetic acid under heating is gradually added dropwise at 75°–80° C. and stirred at the same temperature for 2 hours. After cooling, 200 ml of water is added to the reaction mixture and neutralized with sodium bicarbonate to about pH 6. Insoluble products are filtered off and the obtained solid is extracted with chloroform. The chloroform is distilled off to give a white solid and the obtained white solid is recrystallized from ethanol to give 3,3'-sulfonylbis(docosyl p-hydroxybenzoate), melting at 97°–102° C. (partially contracted and disintegrated above 89° C.).

EXAMPLE 33

To a solution of 45.6 g of benzyl p-hydroxybenzoate, 150 ml of chloroform and 0.5 g of zinc chloride anhydrate is added a solution of 15 g of sulfur monochloride in 20 ml of chloroform at 15° C. and stirred at 40° C. for 5 hours. The precipitated insoluble products are filtered off and the chloroform is distilled off. A solution of the oil thus obtained in ethyl acetate is washed with water, 3N hydrochloric acid, an aqueous sodium bicarbonate solution and then an aqueous sodium chloride solution in turn, and ethyl acetate is distilled off. The obtained residue is purified by a silica gel column chromatography with chloroform to give 3,3'-thiobis(benzyl p-hydroxybenzoate), melting at 145.5°-146.5° C. Then, to a solution of the product thus obtained in acetic acid is gradually added 30% hydrogen peroxide at 70°-80° C. and stirred at the same temperature for several hours. After completion of the reaction, the product is purified to give 3,3'-sulfonylbis(benzyl p-hydroxybenzoate).

EXAMPLE 34

To a mixture of 2-phenylethyl p-hydroxybenzoate, dichloroethane and zinc chloride anhydrate is added a solution of sulfur monochloride in dichloroethane and stirred under heating. The reaction mixture is treated in the same manner as described in the above Examples to give 3,3'-thiobis(2-phenylethyl p-hydroxybenzoate). Further, to a solution of the product thus obtained in acetic acid is gradually added 30% hydrogen peroxide at 70°-80° C. and stirred at the same temperature for 1-2 hours. After completion of the reaction, the product is separated and, if necessary, purified to give 3,3'-sulfonylbis(2-phenylethyl p-hydroxybenzoate).

EXAMPLE 35

To a mixture of 3-phenylpropyl p-hydroxybenzoate, dichloroethane and zinc chloride anhydrate is added a solution of sulfur monochloride in dichloroethane and stirred under heating. The reaction mixture is treated in the same manner as described in the above Examples to give 3,3'-thiobis(3-phenylpropyl p-hydroxybenzoate). Further, to a solution of the product thus obtained in acetic acid is gradually added 30% hydrogen peroxide at 70°-80° C. and stirred at the same temperature for 1-2 hours. After completion of the reaction, the product is separated and, if necessary, purified to give 3,3'-sulfonylbis(3-phenylpropyl p-hydroxybenzoate).

The following compounds can be obtained in a similar manner:
(36) 3,3'-thiobis(tetracosyl p-hydroxybenzoate)
(37) 3,3'-sulfonylbis(tetracosyl p-hydroxybenzoate)
(38) 3,3'-thiobis(hexacosyl p-hydroxybenzoate)
(39) 3,3'sulfonylbis(hexacosyl p-hydroxybenzoate)
(40) 3,3'-thiobis(octacosyl p-hydroxybenzoate)
(41) 3,3'-sulfonylbis(octacosyl p-hydroxybenzoate)
(42) 3,3'-thiobis(4-phenylbutyl p-hydroxybenzoate)
(43) 3,3'-sulfonylbis(4-phenylbutyl p-hydroxybenzoate)
(44) 3,3'-thiobis(5-phenylpentyl p-hydroxybenzoate)
(45) 3,3'-sulfonylbis(5-phenylpentyl p-hydroxybenzoate)
(46) 3,3'-thiobis(6-phenylhexyl p-hydroxybenzoate)
(47) 3,3'-sulfonylbis(6-phenylhexyl p-hydroxybenzoate)

The invention has been fully explained in the description and examples given above, but any variations and modifications thereof may be made without departing from the spirit and scope of the present invention.

We claim:

1. A p-oxybenzoic acid compound of the general formula:

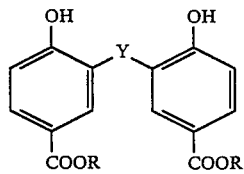

wherein R is alkyl having not less than two carbon atoms or aralkyl and Y is a sulfur atom or sulfonyl with the proviso that R is not butyl if Y is sulfur.

2. The p-oxybenzoic acid compound as claimed in claim 1, wherein R is alkyl having 2-22 carbon atoms or benzyl.

3. The p-oxybenzoic acid compound as claimed in claim 1, wherein the p-oxybenzoic acid compound is 3,3'-thiobis(ethyl p-hydroxybenzoate), 3,3'-sulfonylbis(ethyl p-hydroxybenzoate), 3,3'-thiobis(propyl p-hydroxybenzoate), 3,3'-sulfonylbis(propyl p-hydroxybenzoate), 3,3'-sulfonylbis(butyl p-hydroxybenzoate), 3,3'-thiobis(hexyl p-hydroxybenzoate), 3,3'-thiobis(2-ethylhexyl p-hydroxybenzoate), 3,3'-sulfonylbis(2-ethylhexyl p-hydroxybenzoate), 3,3'-thiobis(dodecyl p-hydroxybenzoate), 3,3'-thiobis(tetradecyl p-hydroxybenzoate), 3,3'-thiobis(hexadecyl p-hydroxybenzoate), 3,3'-sulfonylbis(hexadecyl p-hydroxybenzoate), 3,3'-thiobis(octadecyl p-hydroxybenzoate), 3,3'-sulfonylbis(octadecyl p-hydroxybenzoate), 3,3'-thiobis(docosyl p-hydroxybenzoate), 3,3'-sulfonylbis(docosyl p-hydroxybenzoate) or 3,3'-thiobis(benzyl p-hydroxybenzoate).

* * * * *